United States Patent
McDevitt

(10) Patent No.: US 6,863,530 B2
(45) Date of Patent: Mar. 8, 2005

(54) EXPANDABLE POLYMER DENTAL IMPLANT AND METHOD OF USE

(75) Inventor: Dennis McDevitt, Raleigh, NC (US)

(73) Assignee: Incumed, Inc., Raleigh, NC (US)

( * ) Notice: Subject to any disclaimer, the term of this patent is extended or adjusted under 35 U.S.C. 154(b) by 0 days.

(21) Appl. No.: 10/034,344

(22) Filed: Dec. 28, 2001

(65) Prior Publication Data

US 2003/0124487 A1 Jul. 3, 2003

(51) Int. Cl.$^7$ .............................................. A61C 8/00
(52) U.S. Cl. ...................................................... 433/173
(58) Field of Search ................. 433/172, 173, 433/174, 175, 176, 201.1

(56) References Cited

U.S. PATENT DOCUMENTS

| | | | |
|---|---|---|---|
| 3,435,526 A | * | 4/1969 | Brancato ..................... 433/173 |
| 3,797,113 A | | 3/1974 | Brainin |
| 3,849,887 A | | 11/1974 | Brainin |
| 3,934,347 A | | 1/1976 | Lash |
| 4,186,486 A | | 2/1980 | Gordon |
| 4,199,864 A | | 4/1980 | Ashman |
| 4,244,689 A | | 1/1981 | Ashman |
| 4,270,905 A | | 6/1981 | Mohammed |
| 4,304,553 A | | 12/1981 | Heimke et al. |
| 4,318,696 A | | 3/1982 | Kasama et al. |
| 5,174,755 A | | 12/1992 | Fukuda |
| 5,268,001 A | * | 12/1993 | Nicholson et al. ............ 606/72 |
| 5,350,300 A | | 9/1994 | Gallais |
| 5,425,639 A | | 6/1995 | Anders |
| 5,439,381 A | * | 8/1995 | Cohen ........................ 433/173 |
| 5,492,470 A | * | 2/1996 | Anders ....................... 433/173 |
| 5,527,182 A | | 6/1996 | Willoughby |
| 5,558,517 A | | 9/1996 | Shalaby et al. |
| 5,584,693 A | | 12/1996 | Nishihara |
| 5,759,205 A | | 6/1998 | Valentini |
| 5,766,009 A | | 6/1998 | Jeffcoat |
| 5,782,918 A | | 7/1998 | Klardie et al. |
| 5,873,721 A | | 2/1999 | Willoughby |
| 5,882,351 A | | 3/1999 | Fox |
| 5,931,675 A | * | 8/1999 | Callan ........................ 433/173 |
| 5,996,779 A | | 12/1999 | Klardie et al. |
| 6,007,337 A | * | 12/1999 | Bauer ......................... 433/173 |
| 6,042,380 A | * | 3/2000 | De Rowe .................... 433/173 |
| 6,083,004 A | | 7/2000 | Misch et al. |
| 6,116,070 A | | 9/2000 | Oshida et al. |
| 6,126,445 A | | 10/2000 | Willoughby |
| 6,142,296 A | | 11/2000 | Klardie et al. |
| 6,152,738 A | * | 11/2000 | Aker ........................... 433/173 |
| 6,193,516 B1 | | 2/2001 | Story |
| 6,241,732 B1 | * | 6/2001 | Overaker et al. ............. 606/72 |
| 6,283,753 B1 | | 9/2001 | Willoughby |
| 6,287,310 B1 | | 9/2001 | Fox |
| 6,299,448 B1 | | 10/2001 | Zdrahala et al. |
| 6,431,868 B2 | * | 8/2002 | Story .......................... 433/173 |
| 2001/0000486 A1 | | 4/2001 | Story |

FOREIGN PATENT DOCUMENTS

WO    WO 01/06909 A2    2/2001

* cited by examiner

*Primary Examiner*—Todd E. Manahan
(74) *Attorney, Agent, or Firm*—Ryan Kromholz & Manion, SC

(57) ABSTRACT

Systems and methods for a dental implant system suitable for an endosteal implant into a jawbone are provided. The systems and methods make use of an expandable polymer sheath insertable into a jawbone, an implant insertable into the sheath and causing expansion of the sheath upon insertion, and an abutment adapted to be coupled to the implant and permitting the attachment of a dental prosthesis.

28 Claims, 12 Drawing Sheets

EXPANDABLE POLYMER DENTAL IMPLANT AND METHOD OF USE

FIELD OF THE INVENTION

This invention generally relates to dental implants and methods for installing such implants. rane.

BACKGROUND OF THE INVENTION

Human teeth vary in shape in accordance with their position and function, but share a common structure. As seen in FIG. 1, a tooth 10 consists of a central pulp 12 that communicates with arteries 14, veins 16, and nerves 18. This pulp 12 is surrounded by a calcareous substance known as dentin 20.

As also seen in FIG. 1, the teeth project from sockets 22, or alveoli dentalis, in the alveolar bone 31 of the maxillae (upper jaw) or mandible (lower jaw).

Each socket 22 is a depression in the bone of the jaw lined by a connective tissue known as the periodontal membrane 24. The portion of the tooth 10 that actually fits into the socket 22 is formed into one or more roots 26. The root 26 is joined to the periodontal membrane 24 and held into the socket 22 by a calcified connective tissue known as the cementum 28. The periodontal membrane 24 serves as a "shock absorber" during the mastication (chewing) process.

The projecting portion of a tooth 10, known as the crown 11, comprises grinding surfaces and is covered by another calicified connective tissue known as enamel 30.

The gums 32, or gingival tissue, covers the base of the crown 11 and project between adjacent surfaces of the teeth 10. Normal, healthy gum tissue 32 serves to anchor teeth in place, as illustrated in FIG. 2.

Gum disease, or periodontal disease, is an inflammation or infection of the gingival tissue. Periodontal disease is caused by a sticky film of bacteria, called placque. Over time, placque hardens into calculus (tartar).

Mild inflammation, characterized by red, swollen, and bleeding gums 32, is known as gingivitis. Poor oral hygiene is the primary cause of gingivitis. This early stage of periodontal disease is reversible with proper professional care and good oral home care.

If left untreated, the disease spreads to other supporting structures including alveolar bone 31, producing a more advanced stage of periodontal disease known as periodontitis.

Periodontitis, illustrated in FIG. 3, results in the destruction of alveolar bone 31 and the periodontal membrane 24. This stage is characterized by the gums 32 receding or pulling away from the teeth, resulting in the formation of pockets between the teeth and gums 32.

As the disease progresses, teeth become loose, often necessitating extraction. Thus, periodontal disease is a major cause of tooth loss.

A variety of conditions have been found to contribute the development and advancement of periodontal disease, including tobacco use, genetics, pregnancy, puberty, stress, medications, clenching or grinding of teeth, diabetes, and poor nutrition.

Because of the widespread nature of the disease, there have been a variety of methods devised to implant and secure a dental prosthesis.

The most common type of implant is endosseous, in which a screw or similar device is inserted beneath the jawbone. The device serves to mimic a root structure and protrudes through the gum to hold a prosthesis.

However, when an endosteal implant is not possible due to minimal bone height, a subperiosteal implant can be placed on top of the jaw with the metal framework's posts protruding through the gum to hold the prosthesis.

A conventional prior art endosteal implant system 100, depicted in FIG. 4, typically comprises an implant 110, an inserting device 120, a closure screw 130, and an abutment 140 adapted to receive a dental prosthesis 150.

Conventional implants 110 are cylindrically-shaped members commonly made of rigid, non-expandable biocompatible materials, e.g., a metallic alloy (e.g., titanium alloy) or ceramic (e.g., $Al_2O_3$).

The material can also permit osteo ingrowth (growth of bony tissue), also known as ankylosis, into the implant 110.

The implant 110 may be of a hollow or solid nature. A hollow nature further encourages osteo ingrowth into the implant 110. In either a hollow or solid arrangement, the top portion of the implant 110 protrudes above the gum line and is adapted to receive the closure screw 130 and the abutment 140. The implant 110 may additionally contain holes penetrating the wall of the implant to further promote osteo ingrowth.

The inserting device 120 is a tool adapted to couple the implant 110 and aid in the insertion of the implant 110 within the jawbone 160.

The closure screw 130 is a screw adapted to fit within the top portion of the implant 110. The closure screw 130 serves to cover and protect the top portion of the implant 110 after insertion into the jawbone 160 and prior to attachment of the abutment 140.

The abutment 140 is adapted to fit within the top portion of the implant 110. The abutment 140 serves to permit attachment of a dental prosthesis 150.

In use, the system 110 is employed in a two-part procedure. In the first part of the procedure, the site is prepared for the insertion of the implant 110 by conventional techniques.

As shown in FIG. 5A, the implant 110 is then inserted into a predrilled hole 170 (represented by phantom lines in FIGS. 5A–5D) within the jawbone 160 by using the inserting device 120 to screw (represented by arrow in FIG. 5A) the implant 110 into the jawbone 160 (e.g., with the aid of a ratchet).

The inserted implant 110 is shown in FIG. 5B. Next, as also shown in FIG. 5B, the closure screw 130 is then screwed (represented by arrow in FIG. 5B) into the top portion of the implant 110.

The first part of the procedure is then complete. The second part of the procedure is performed desirably at least several weeks later. This waiting period permits time for osteo (bone) ingrowth into the implant 110. This process however does not reestablish the periodontal membrane/ligament that was destroyed as a result of the tooth loss. The contact between the implant and the bone is a rigid connection with no dampening effect.

After the appropriate waiting period, the second part of the procedure is then performed. First, the closure screw 130 is removed (not shown).

Second, as illustrated in FIG. 5C, the abutment 140 is screwed (represented by arrow in FIG. 5C) into the top portion of the implant 110.

Finally, as shown in FIG. 5D, a conventional dental prosthesis 150 is attached to the abutment 140 using conventional techniques.

As the prior art illustrates, conventional ankylosing implants require the procedure to be at least two-step and require more than one office visit.

The need remains for a straightforward, cost effective dental implant that can be inserted easily and with a minimal number of procedures or office visits. Further, the need remains for an implant that provides stability, comfort, and long-term wear.

SUMMARY OF THE INVENTION

Improved dental implant systems and methods of use are provided. The systems and methods utilize an expandable polymer sheath suitable for placement within a jawbone. The sheath serves as an artificial periodontal membrane. A rigid implant is inserted within the polymer sheath and causes expansion of the polymer sheath when fitted within the sheath. An abutment is provided to couple the rigid implant and permits attachment of a dental prosthesis. The dental prosthesis can be for a single tooth or extend as a bridge over a gap.

The systems and methods also make possible the ability to post-operatively remove the implant in the event that modifications need to be made. Removal of the traditional metallic implant is very difficult due to osteo in-growth and once removed the replacement requires another waiting period for proper in-growth to take place.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention that may be embodied in other specific structures.

Dental Implant With Expandable Polymer Sheath

Figure 6:
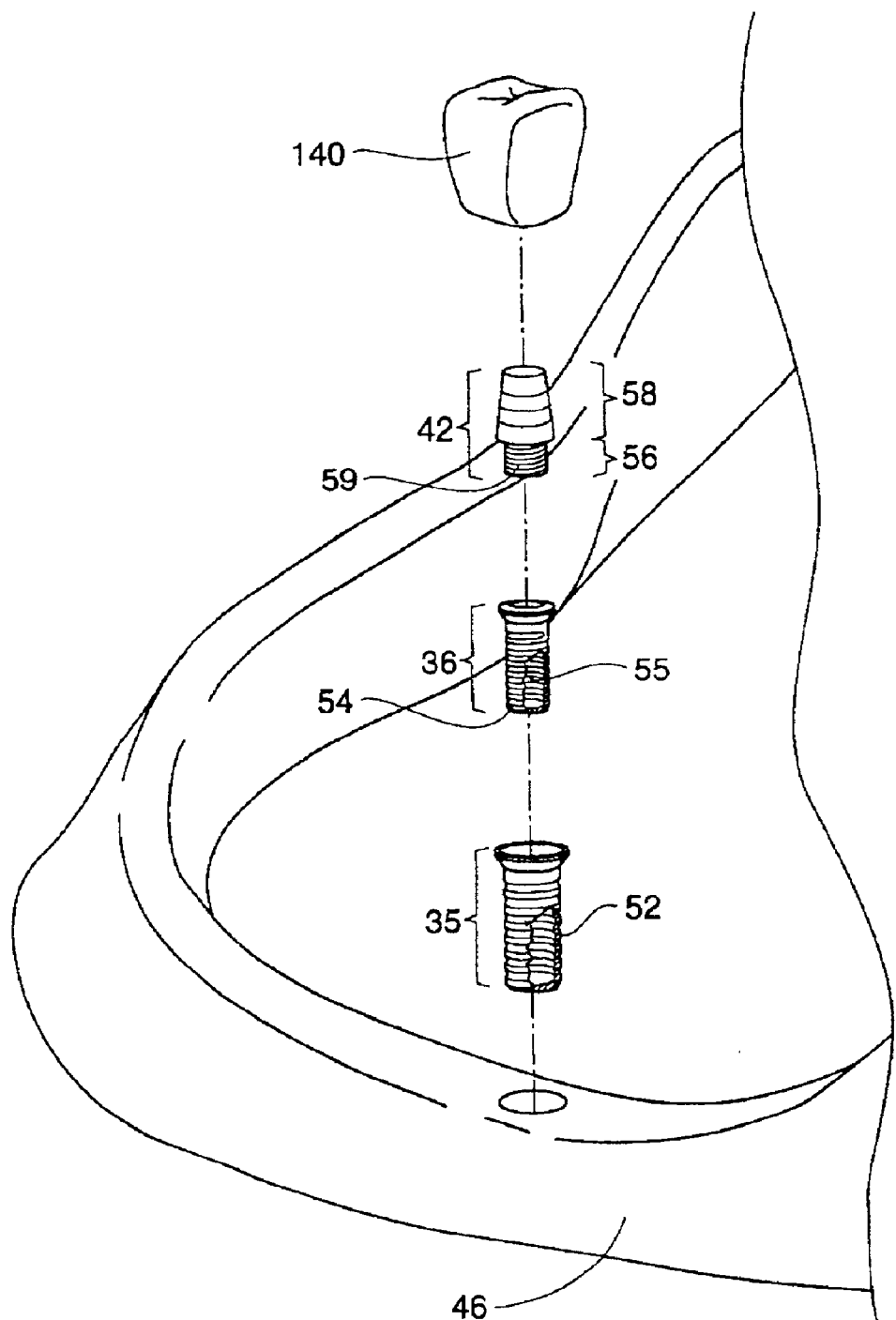
FIG. 6 is a perspective view of a portion of a lower human jawbone, showing, in an exploded view, a dental implant system incorporating features of the invention.

FIG. 6 shows a dental implant system 34 suitable for an endosteal implant into a jawbone 46. The system comprises an expandable polymer sheath 35, an implant 36, and an abutment permitting the attachment of a dental prosthesis 44. Details of each of these system components will now be described in detail.

A. The Expandable Polymer Sheath

As seen in FIG. 6, the system 34 provides an expandable polymer sheath 35. The sheath 35 serves to receive the implant 36 and provides an artificial periodontal membrane 24, i.e., the sheath 35 mimics the periodontal membrane 24 by performing a like cushioning function.

The sheath 35 is a hollow cylindrical body having a closed bottom end portion and an open top end portion. The open top portion serves to receive the implant 36.

The expandable nature of the sheath 35 permits it to receive the implant 36. Toward this end, the inner diameter of the sheath 35 is slightly less than the outer diameter of the implant 36, resulting in expansion of the sheath 35 upon insertion of the implant 36. This expansion further serves to secure the sheath 35 and implant 36 within the jawbone 46.

Figure 7A:
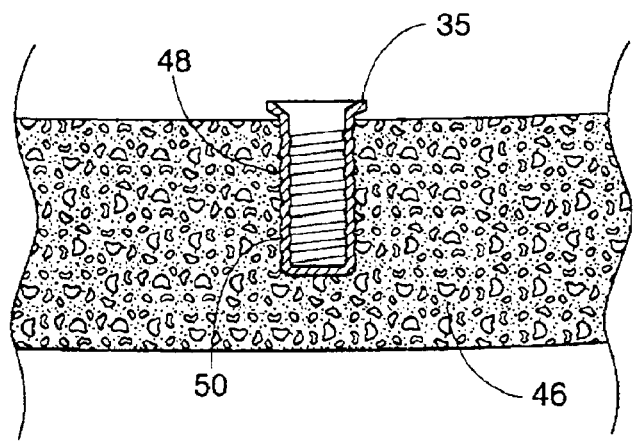
FIGS. 7A–7C are side sectional views of a human jawbone showing the expansion of the polymer sheath component of the system shown in FIG. 6 upon insertion of the implant component into the jawbone.
Figure 7B:
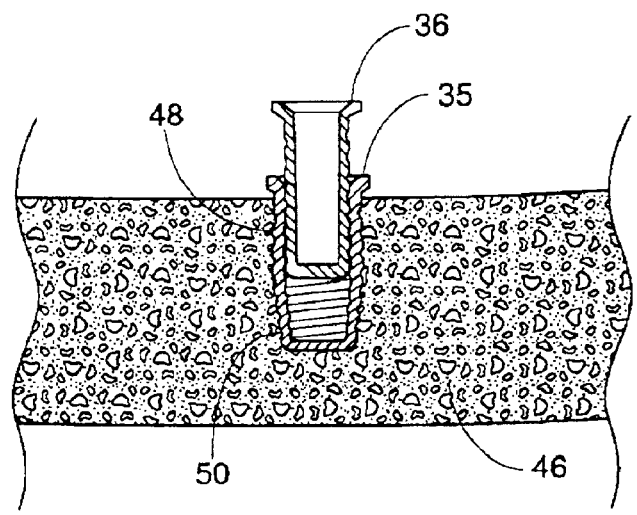
Figure 7C:
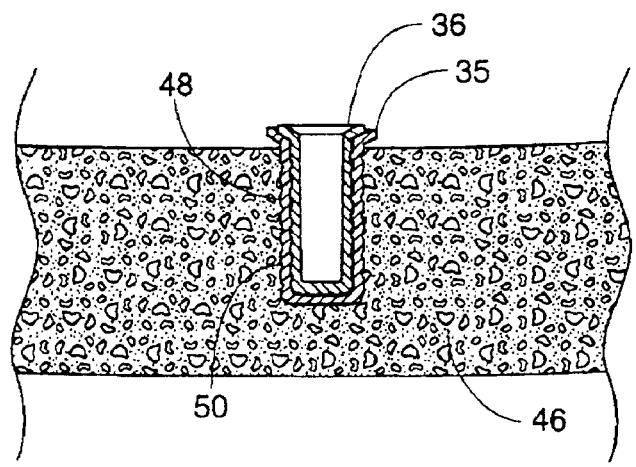

FIGS. 7A–7C detail this expansion process. FIG. 7A illustrates a polymer sheath 35 inserted in a jawbone 46. FIG. 7B shows the expansion of the sheath 35 upon insertion of an implant 36. FIG. 11C shows the implant 36 inserted into the expanded sheath 35.

Suitable materials for the sheath 35 include Ultra High Molecular Weight Polyethylene, High Density Polyethylene (HDPE), Polyurethane Elastomer, and Polypropylene.

As also seen in FIGS. 6 and 7A–7C, the outer surface of the sheath 35 contains ribs 48. Expansion of the sheath 35 (see FIGS. 7A–7C) compresses surrounding bone structure, further securing and anchoring the sheath 35 within the jawbone 46. The ribs 48 also serve to promote osteo ingrowth, as bony tissue can grow into the grooves 50 between the ribs 48.

In a representative embodiment, the ribs 48 are approximately 0.005"–0.020" deep on a sheath 35 that has about a 0.120"–0.200" outside diameter. The rib 48 design could be straight or threaded and could also be intermittent.

As the expansion of the sheath 35 and the ribs 48 serve to anchor the sheath 35 within the jawbone 46 at the time of insertion, it is not necessary to provide a waiting period after insertion of the implant 36 to permit osteo ingrowth.

Optionally, the sheath 35 can contain holes that penetrate the sheath 35 wall to further permit osteo ingrowth (not shown). Desirably, the sheath 35 does not contain holes, as holes would reduce the total surface area of the artificial periodontal membrane 24.

Also optionally, as seen in FIG. 6, the sheath 35 can include internal threads 52 capable of mating with external threads 54 on the outer surface of the implant 36. These threads serve to further secure the implant 36 within the sheath 35.

B. The Implant

As also shown in FIG. 6, the system also provides an implant 36. The implant 36 is a generally cylindrical member insertable into the sheath 35 and causes expansion of the sheath 35 upon insertion. The expansion further secures the sheath 35 within the jawbone 46, as previously noted.

The implant 36 is a solid, rigid, and non-expandable member, thereby providing stability and strength to the sheath 35 when inserted into the sheath 35.

The implant 36 is adapted to mate with the abutment 42. In the embodiment illustrated in FIG. 6, the implant 36 has internal threads 55 that serve to receive the abutment 42.

Figure 1:
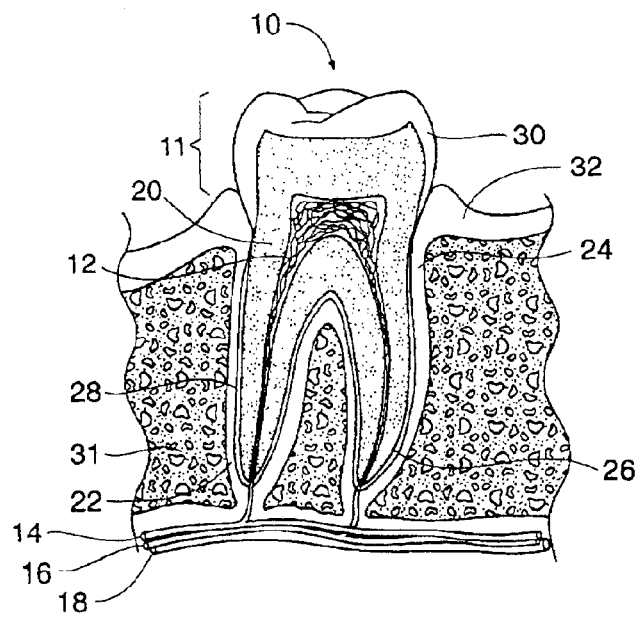
FIG. 1 is a sectional view of a normal human tooth.
Figure 2:
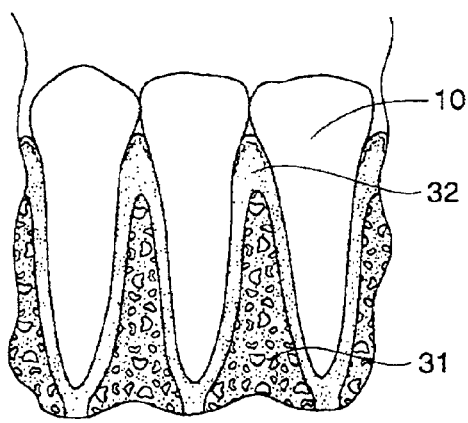
FIG. 2 is a sectional view, with portions removed, of normal, healthy teeth and gums.
Figure 3:
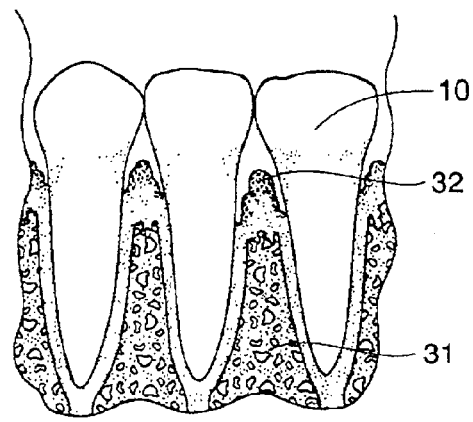
FIG. 3 is a view similar to that shown in FIG. 2 and further illustrating the effects of periodontitis on the teeth and gums.
Figure 4:
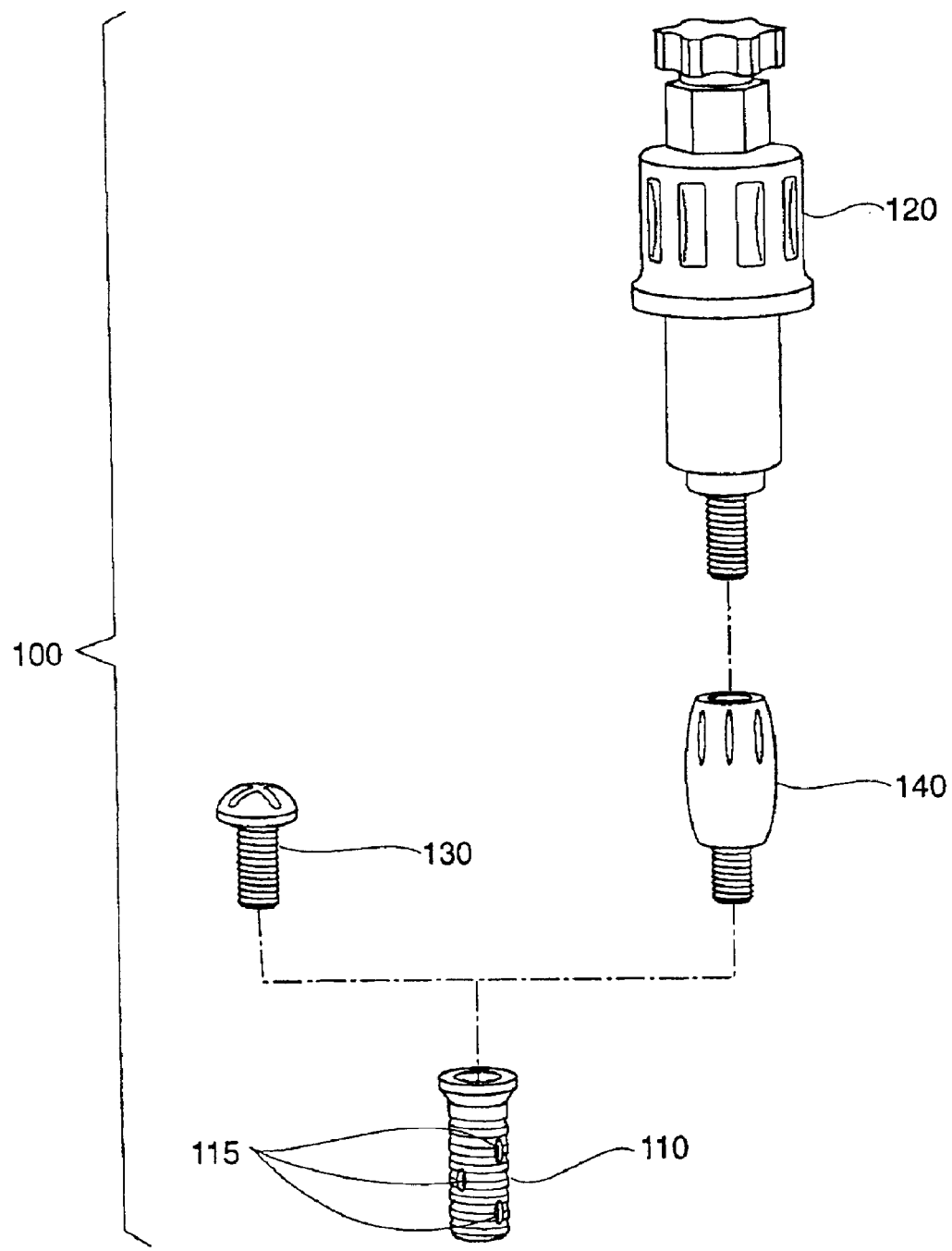
FIG. 4 is an exploded perspective view of a prior art dental implant system.
Figure 5A:
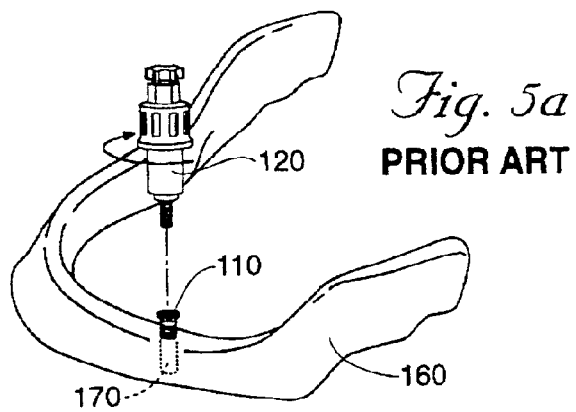
FIGS. 5A–5D are schematic perspective views of a lower human jawbone illustratating the use of the components of the prior art system shown in FIG. 4.
Figure 5B:
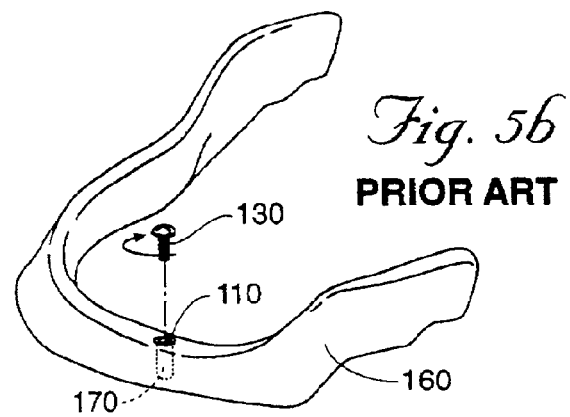
Figure 5C:
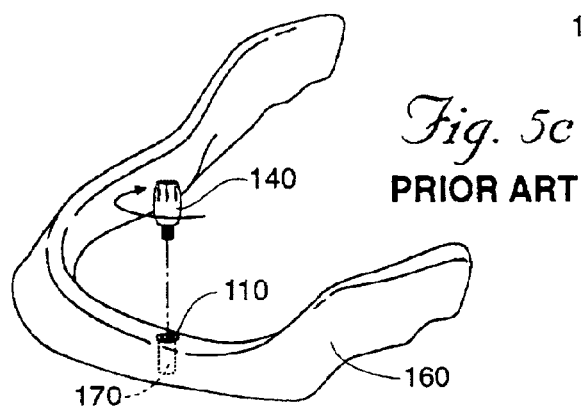
Figure 5D:
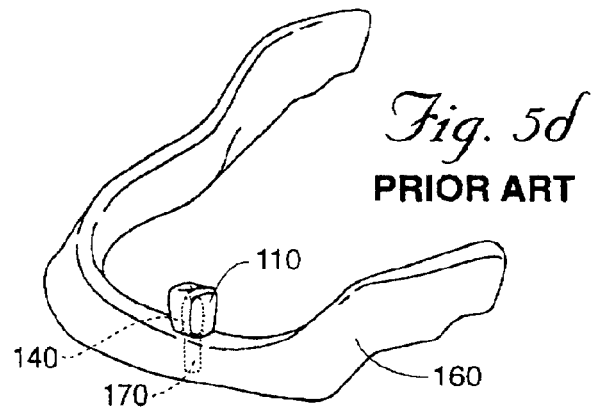

Thus, the implant 36 serves to mimic the tooth root 26 by providing a stabilizing structure to which an abutment 42 and prosthesis 44, together mimicking a tooth crown 11 (see also FIG. 1), are secured within the jawbone 46.

The implant 36 can be adapted to be inserted into the sheath 35 in variety of ways. For example, as shown in FIG. 6, the implant 36 can be provided with external threads 54. In this arrangement, the external threads 54 are adapted to mate with internal threads 52 of the sheath 35. In this arrangement, insertion of the implant 36 is by screwing the implant 36 into the sheath 35.

In an alternate embodiment, the implant 36 does not contain external threads 54. In this arrangement, the implant 36 has an exterior surface that has a Morse taper or that is ribbed, or both. In either of these embodiments, tapered or ribbed, insertion of the implant 36 is by frictional engagement (i.e., "pressing" of the implant 36 into the sheath 35).

Suitable materials for the implant 36 include inert materials suitable for implantation in the body, e.g., titanium alloy or a stainless steel alloy.

C. The Abutment

As further shown in FIG. 6, the system also provides an abutment 42. The abutment 42 is a solid member adapted to mate with the implant 36. The abutment 42 has a first region 56 and a second region 58.

In the embodiment illustrated in FIG. 6, the first region 56 is cylindrical and includes external threads adapted to mate with the internal threads 55 of the implant 36. If desired, a conventional dental cement can be additionally applied to further secure the abutment 42 within the implant 36. The second region 58 includes a Morse taper away from the first region 56 and serves to receive the prosthesis 44.

Suitable materials for the abutment 42 include, but are not limited to, titanium or titanium alloys.

In a representative embodiment, the polymer sheath 35 is made of HDPE and is 12 mm×4 mm outer diameter, the implant 36 is made of Titanium and is 11 mm×3.5 mm outer diameter, and the abutment 42 is made of Titanium and is 5 mm×3 mm outer diameter.

II. Use of Implant

The system 34 can be employed in the replacement of either a single tooth or of multiple teeth, as will now be described. While periodontal disease is a primary cause of tooth loss, it should be understood that the system 34 is suitable to treat tooth loss resulting from other causes.

A. Use in Replacement of Single Tooth

In using the system 34 in the replacement of a single tooth, the site is first prepared by conventional techniques.

Figure 8:
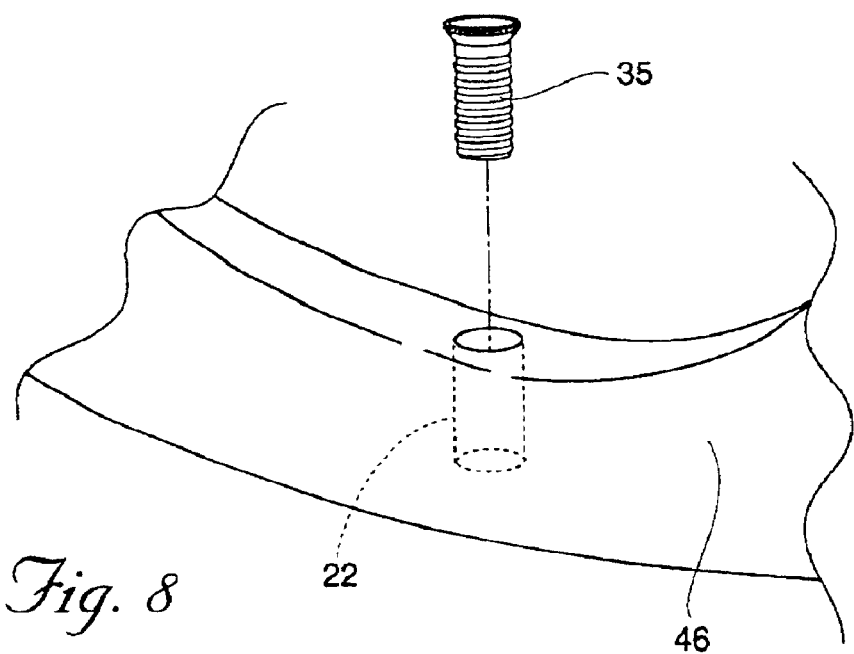
FIG. 8 is a side perspective view of a portion of a lower human jawbone showing the insertion of the polymer sheath component of the system shown in FIG. 6 into the jawbone.

Next, as seen in FIG. 8, the polymer sheath 35 is inserted (depicted by dot-dash line in FIG. 8) into the prepared site, e.g., by use of a mandrel.

Figure 9:
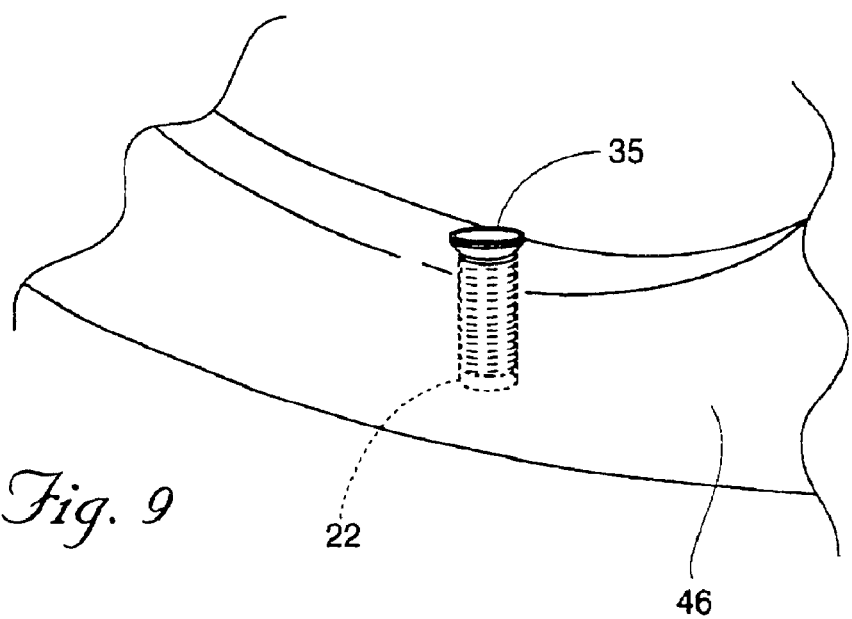
FIG. 9 is a view similar to FIG. 8 showing the polymer sheath inserted into the jawbone.

FIG. 9 illustrates a polymer sheath 35 after insertion into a jawbone 46.

Figure 10:
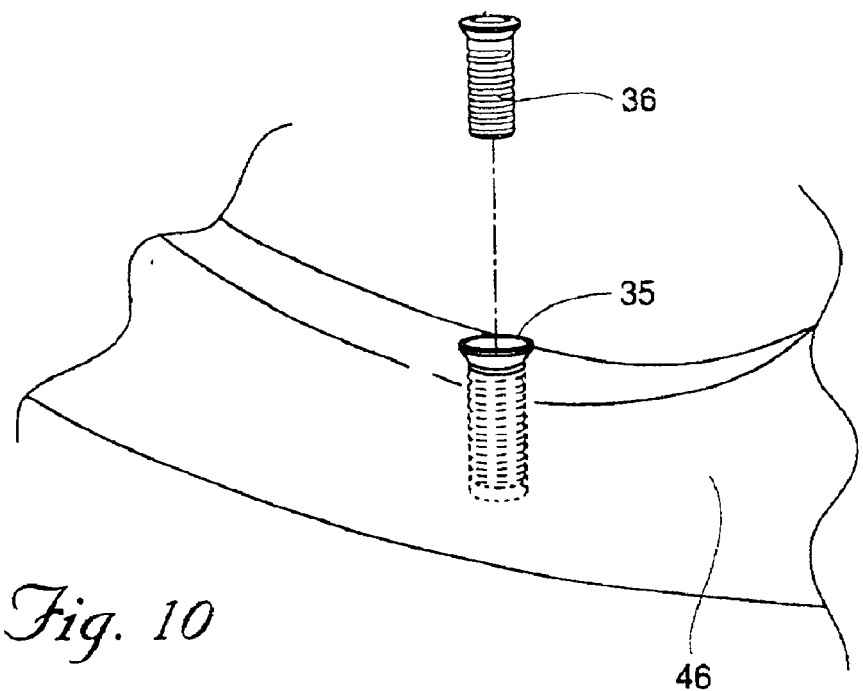
FIG. 10 is a view similar to FIG. 9 showing the insertion of the implant component of the system shown in FIG. 6 into the polymer sheath.

Then, as shown in FIG. 10, the implant 36 is inserted (depicted by dot-dash line in FIG. 10). As previously noted, the implant 36 can include external threads 54 or an exterior surface that is tapered or ribbed (not shown).

If the implant 36 includes external threads 54, the implant 36 is screwed into the sheath 35 with the use of a tool, e.g., a screwdriver.

If the implant 36 includes a tapered or ribbed surface, the implant 36 is inserted by frictional engagement, e.g., pressing with the aid of a mandrel. The implant 36 is thereby compressed into the sheath 35 which secures it in the sheath 35 and to the bone 46 via the compression forces exerted from the elastic polymer sheath 35.

Figure 11:
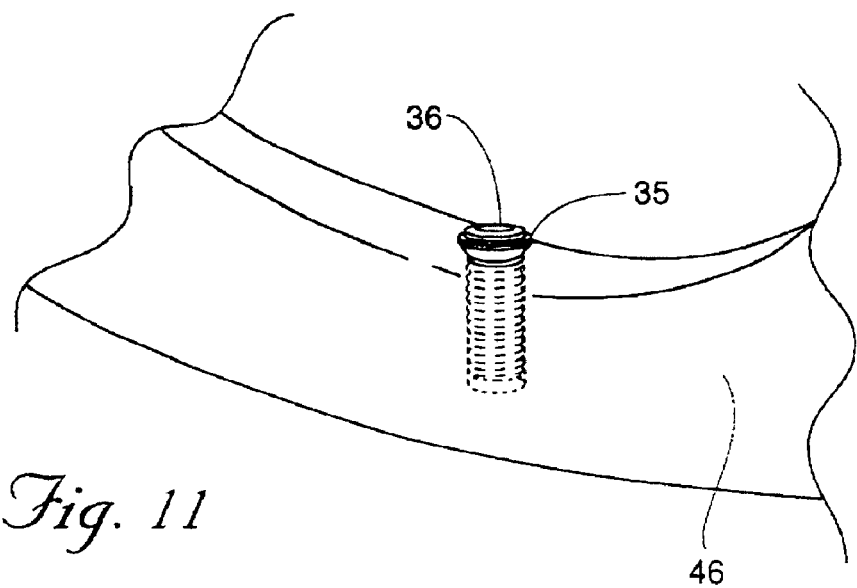
FIG. 11 is a view similar to FIG. 10 showing the implant inserted into the polymer sheath.

FIG. 11 illustrates an implant 36 after insertion into a sheath 35 within a jawbone 46.

Figure 12:
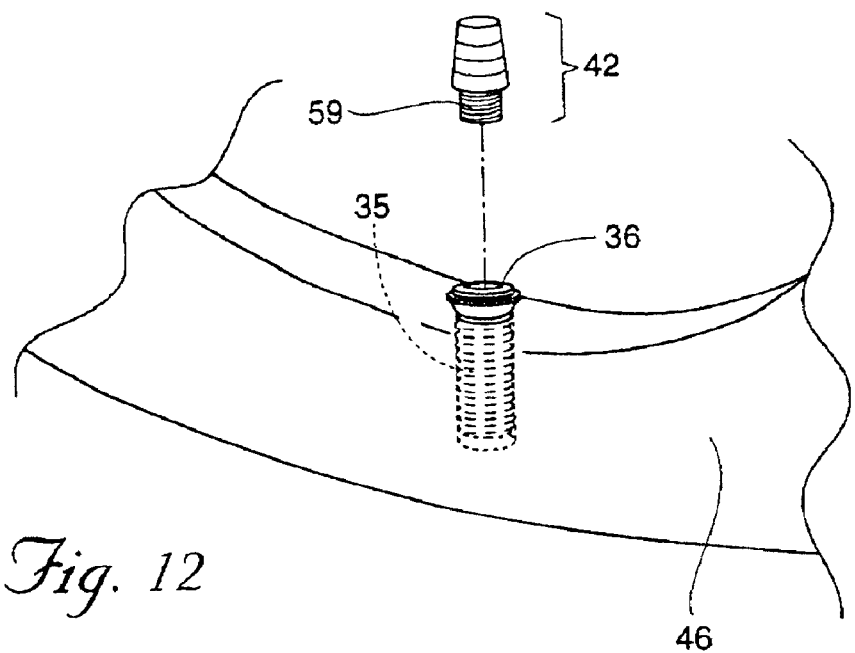
FIG. 12 is a view similar to FIG. 11 showing the coupling of the abutment component of the system shown in FIG. 6 with the implant.

Next, as shown in FIG. 12, the abutment 42 is inserted (depicted by dot-dash line in FIG. 12) into the implant 36, e.g., by screwing the threaded first region 56 into the threaded top end portion of the implant 36.

Figure 13:
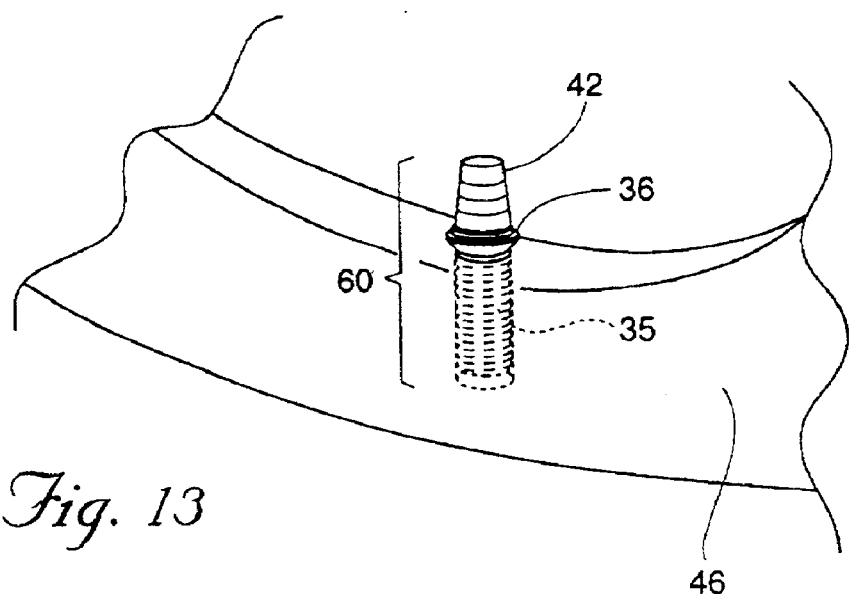
FIG. 13 is a view similar to FIG. 12 showing the abutment component coupled to the implant.

FIG. 13 illustrates an abutment 42, implant 36, and sheath 35 after insertion into a jawbone 46. Together, the abutment 42, implant 36, and sheath 35 form a support structure 60 for securing a dental prosthesis 44.

Figure 14:
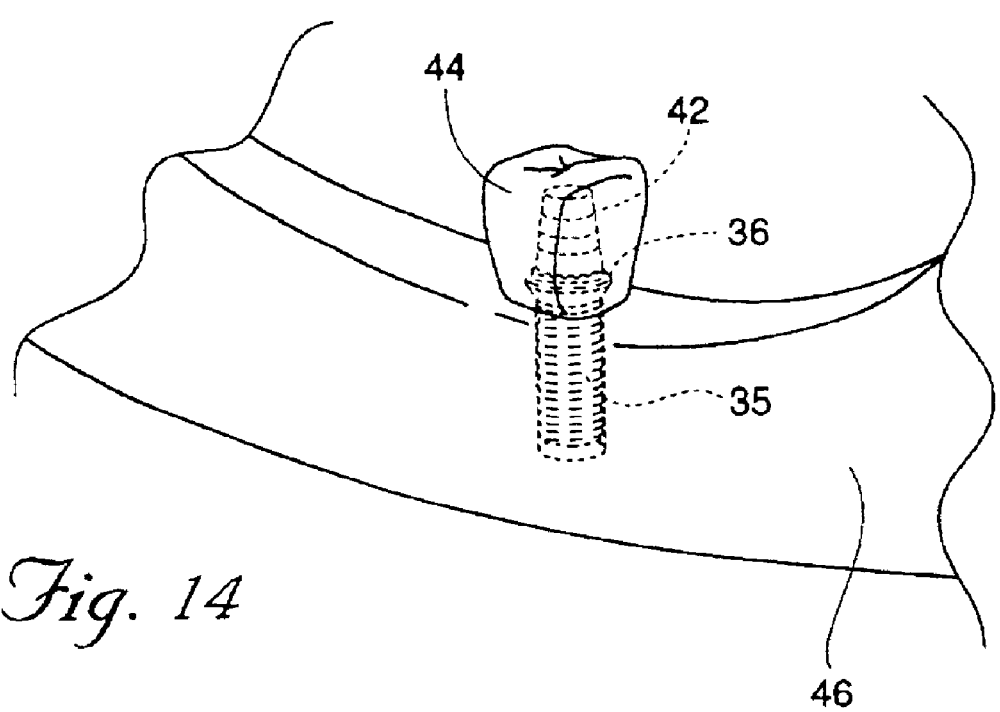
FIG. 14 is a view similar to FIG. 13 showing a dental prosthesis attached to the abutment.

Finally, as FIG. 14 shows, a dental prosthesis 44 is attached to the abutment 42 using conventional techniques.

As no waiting period is needed to allow for osteo ingrowth, the system 34 provides for the insertion of the sheath 35, implant 36, and abutment 42 and the attachment of a prosthesis 44 all within a single office visit. This results in both time and cost savings.

In some cases, it may be desirable to carry out the described procedure over multiple office visits to allow the gum and soft tissue time to heal prior to installing the prosthesis 44. In this case, the sheath 35 and implant 36 can be inserted in the first office visit. A cover screw is then inserted into the implant 36 to cover and protect the implant 36 between office visits (not shown). The abutment 42 can then be inserted and prosthesis 44 attached during a subsequent visit or visits.

B. Use of System in Replacement of Multiple Teeth

While use of the system 34 has been described in relation to the replacement of a single tooth, it is often necessary to replace multiple teeth or an entire set of teeth.

Use of the system 34 when a person is missing multiple teeth (partially edentulous) will now be described.

Figure 15A:
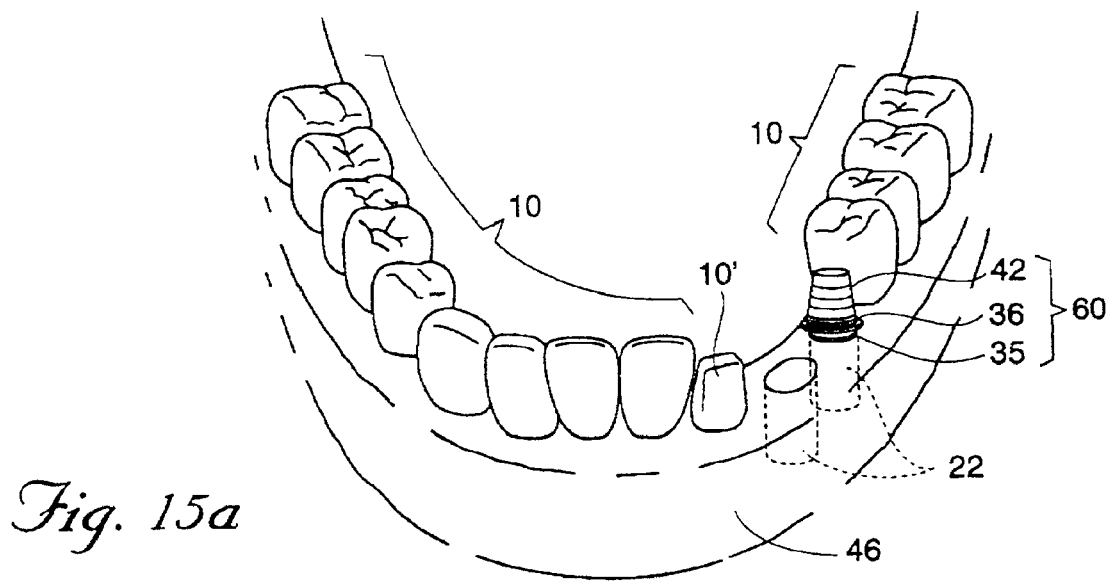
FIGS. 15A and 15B are front perspective views of a lower human jaw bone having a gap of missing teeth and further showing the use of the system shown FIG. 6 in a procedure for the insertion of a dental bridge to fill the gap.
Figure 15B:
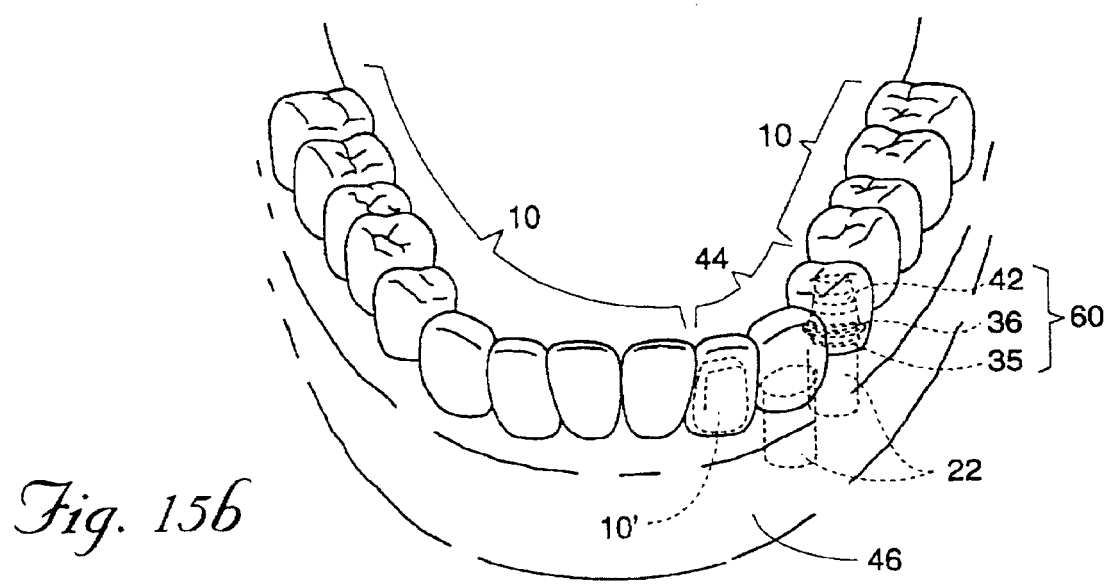

FIGS. 15A and 15B illustrate the use of the system 34 with bridgework (see also FIG. 6). Multiple teeth are commonly replaced using bridgework. For example, a prosthesis 44 covering a gap caused by multiple missing teeth can be anchored at one end by an abutment 42 and at another end by adhesion to a prepared natural tooth 10'. Typically, the prepared natural tooth 10' is prepared by removal of a portion of enamel 30 and dentin 20 (see also FIG. 1). The prosthesis 44, anchored at both ends, serves as a "bridge" over the gap.

As FIG. 15A shows, a support structure 60 is inserted into the socket 22 of a missing tooth (depicted by phantom lines in FIGS. 14A and 14B) at one end of the gap, as previously described.

As FIG. 15B illustrates, a prosthesis 44 is adhesively attached, using conventional techniques, at one end to the abutment 42 and at the other end to a prepared natural tooth 10' at the opposite end of the gap. Thus, the prosthesis 44 extends over the gap to form a bridge.

Figure 16A:
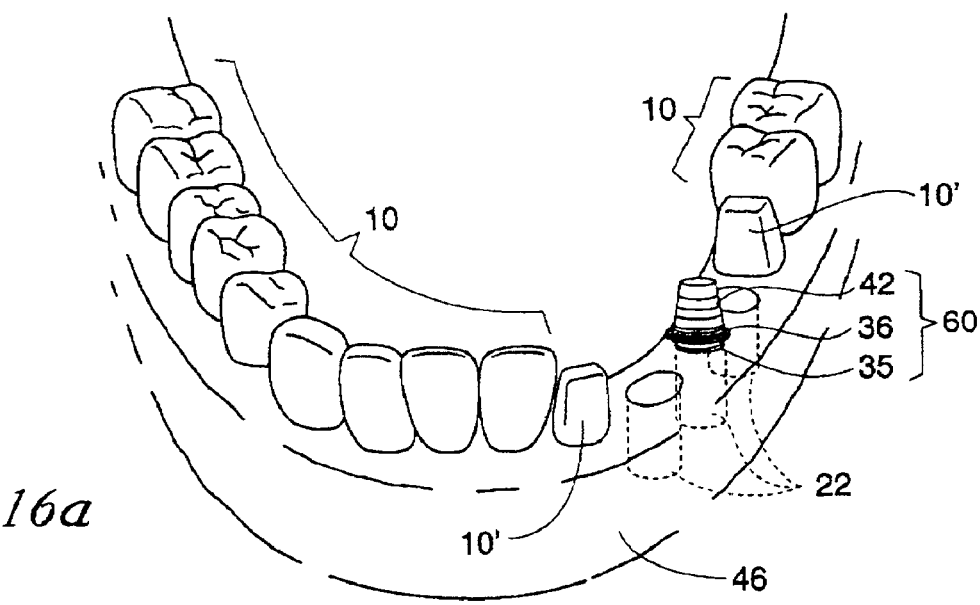
FIGS. 16A and 16B are front perspective views of a lower human jaw bone having a gap of missing teeth and further showing the use of the system shown FIG. 6 in an alternative procedure for the insertion of a dental bridge.
Figure 16B:
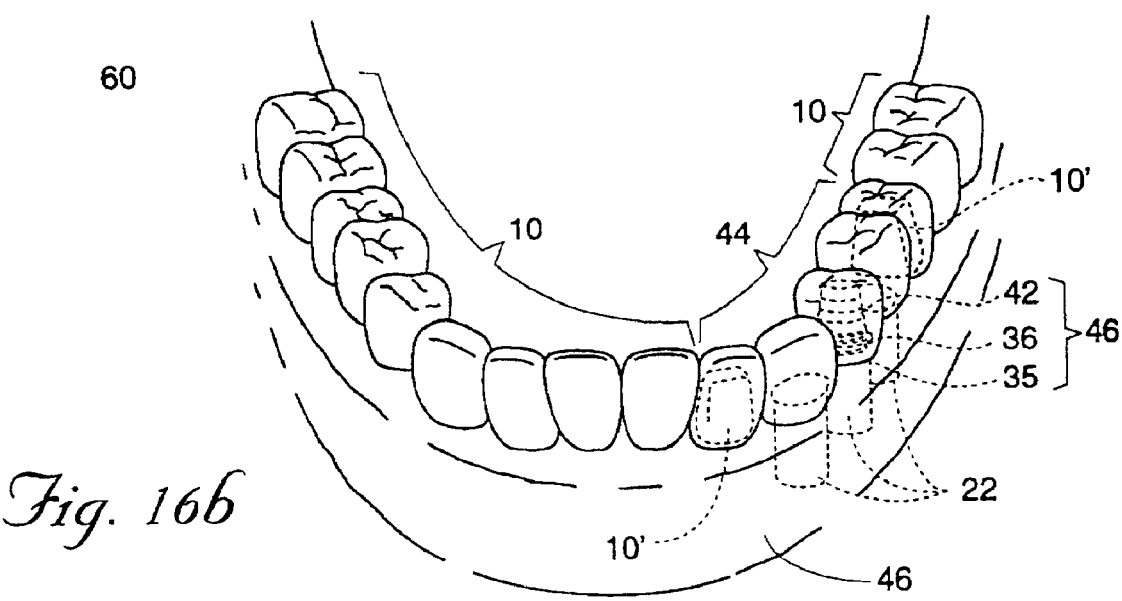

Alternately, as illustrated in FIGS. 16A and 16B, the system 34 can be employed to cover an extended gap. As FIG. 16A shows, the support structure 60 is placed in the socket 22 of missing tooth (depicted by phantom lines in FIGS. 16A and 16B) in the center of a large gap.

As seen in FIG. 16B, the prosthesis 44 is anchored in the center by the abutment 42 and attached at each end to a prepared natural tooth 10' by conventional techniques.

Figure 17A:
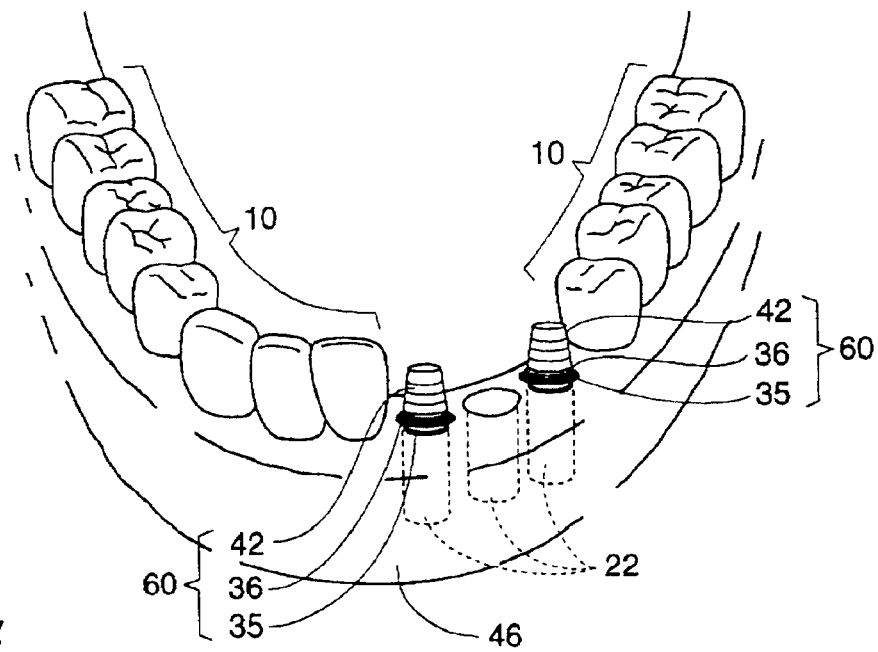
FIGS. 17A and 17B are front perspective views of a lower human jaw bone having a gap of missing teeth and further showing the use of the system shown FIG. 6 in an another alternative procedure for the insertion of a dental bridge.
Figure 17B:
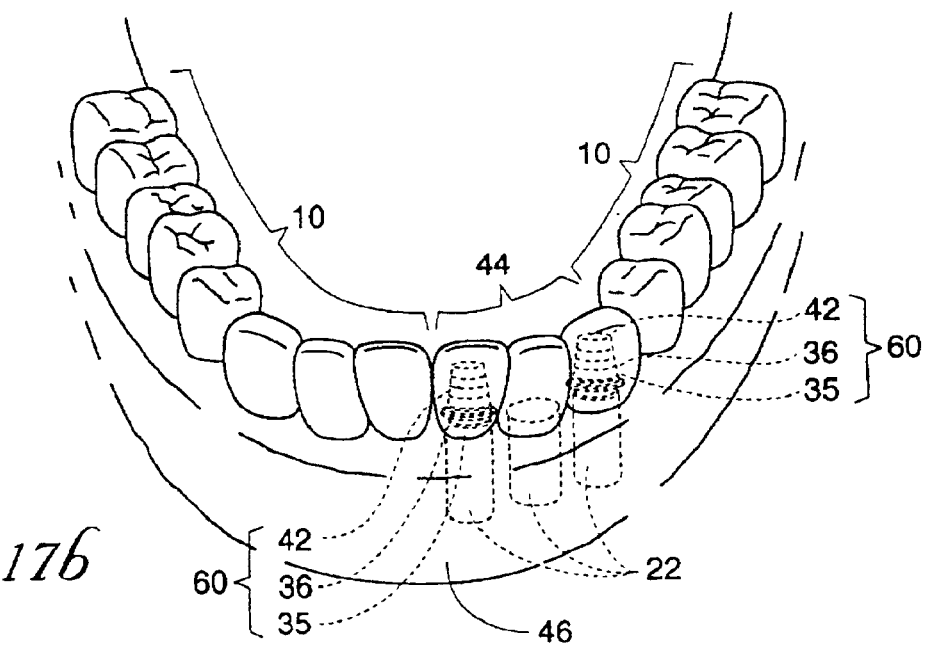

In an alternate arrangement, illustrated in FIGS. 17A and 17B, multiple support structures 60 can be employed to assist in covering a large gap.

As FIG. 17A shows, two support structures 60 are placed in the sockets 22 of missing teeth (depicted by phantom lines in FIGS. 17A and 17B) at opposite ends of a large gap.

As seen in FIG. 17B, the prosthesis 44 is anchored at each end by an abutment 42, as previously described.

The above illustrations of use of the system 34 with bridgework are merely illustrative. It is to be understood that the system 34 can be employed in a variety of other bridgework techniques.

The above described embodiments of this invention are merely descriptive of its principles and are not to be limited. The scope of this invention instead shall be determined from the scope of the following claims, including their equivalents.

What is claimed is:

1. A dental implant system that bears compressive mastication load conditions after installation, the system comprising
    a rigid implant including a connector sized and configured to be attached to a dental prosthesis,
    an expandable polymer sheath suitable for placement within a jawbone, the sheath including polymer material means for functioning as an artificial periodontal membrane; and
    the rigid implant being sized and configured to fit within the polymer sheath, the polymer material means being operative for expanding and thereby compressing surrounding jawbone structure in response to fitment of the rigid implant and, while in compression, for bearing compressive mastication load conditions.

2. A dental implant system that bears compressive mastication load conditions after installation without a presence of osteo ingrowth, the system comprising
    a rigid implant including a connector sized and configured to be attached to a dental prosthesis,
    an expandable polymer sheath suitable for placement within a jawbone, the sheath including polymer material means for functioning as an artificial periodontal membrane; and
    the rigid implant being sized and configured to fit within the polymer sheath, the polymer material means being operative for expanding and thereby compressing surrounding jawbone structure in response to fitment of the rigid implant and, while in compression, for bearing compressive mastication load conditions without a presence of osteo ingrowth.

3. A method of installing a dental prosthesis comprising the steps of:
    providing a system as in claim 2;
    providing a dental prosthesis;
    preparing a site within a jawbone;
    inserting the polymer sheath into the prepared site;
    inserting the implant within the sheath, thereby causing expansion of the polymer material means within the jawbone; and
    attaching the dental prosthesis to the connector.

4. A method as in claim 3 wherein the dental prosthesis is a crown.

5. A method as in claim 3 wherein the dental prosthesis is a bridge.

6. A system as in claim 1 or 2
    wherein the polymer material means includes Ultra High Molecular Weight Polyethylene.

7. A system as in claim 1 or 2
    wherein the polymer material means includes Polypropylene.

8. A system as in claim 1 or 2
    wherein the polymer material means includes High Density Polyethylene.

9. A system as in claim 1 or 2
    wherein the polymer material means includes Polyurethane Elastomer.

10. A system as in claim 1 or 2
    wherein the implant is made of titanium or an alloy thereof.

11. A system as in claim 1 or 2
    wherein the implant is made of stainless steel or an alloy thereof.

12. A system as in claim 1 or 2
    wherein the polymer sheath has an exterior surface that is ribbed.

13. A system as in claim 1 or 2
    wherein the polymer sheath has an interior surface that is threaded, and
    wherein the implant has an exterior surface that is threaded, and
    whereby the interior surface of the polymer sheath mates with the exterior surface of the implant when the implant is fitted within the polymer sheath.

14. A system as in claim 1 or 2
    wherein the implant is tapered.

15. A system as in claim 1 or 2
    wherein the implant is ribbed.

16. A dental implant system that bears compressive mastication load conditions after installation, the system comprising
    a dental prosthesis,
    a rigid implant including a connector sized and configured to be attached to the dental prosthesis,
    an expandable polymer sheath suitable for placement within a jawbone, the sheath including polymer material means for functioning as an artificial periodontal membrane; and
    the rigid implant being sized and configured to fit within the polymer sheath, the polymer material means being operative for expanding into compression within the jawbone in response to fitment of the rigid implant and for bearing compressive mastication load conditions on the dental prosthesis.

17. A dental implant system that bears compressive mastication load conditions after installation without a presence of osteo growth, the system comprising
- a dental prosthesis,
- a rigid implant including a connector sized and configured to be attached to the dental prosthesis,
- an expandable polymer sheath suitable for placement within a jawbone, the sheath including polymer material means for functioning as an artificial periodontal membrane; and
- the rigid implant being sized and configured to fit within the polymer sheath, the polymer material means being operative for expanding into compression within the jawbone in response to fitment of the rigid implant and for bearing compressive mastication load conditions on the dental prosthesis without a presence of osteo ingrowth.

18. A system as in claim 16 or 17
wherein the dental prosthesis is a single crown.

19. A system as in claim 16 or 17
wherein the dental prosthesis is a bridge.

20. A method of installing a dental prosthesis comprising the steps of:
- providing a system as in claim 1;
- providing a dental prosthesis;
- preparing a site within a jawbone;
- inserting the polymer sheath into the prepared site;
- inserting the implant within the sheath, thereby causing expansion of the polymer material means within the jawbone; and
- attaching the dental prosthesis to the connector.

21. A method as in claim 20
wherein the dental prosthesis is a crown.

22. A method as in claim 20
wherein the dental prosthesis is a bridge.

23. A dental implant that bears compressive mastication load conditions after installation, the implant comprising an expandable polymer sheath suitable for placement within a jawbone, the sheath including polymer material means for functioning as an artificial periodontal membrane, the polymer material means further being operative for expanding and thereby compressing surrounding jawbone structure in response to fitment of a rigid body into the sheath and, while in compression, for bearing compressive mastication load conditions.

24. A dental implant that bears compressive mastication load conditions after installation without a presence of osteo ingrowth, the implant comprising an expandable polymer sheath suitable for placement within a jawbone, the sheath including polymer material means for functioning as an artificial periodontal membrane, the polymer material means further being operative for expanding and thereby compressing surrounding jawbone structure in response to fitment of a rigid body into the sheath and, while in compression, for bearing compressive mastication load conditions without a presence of osteo ingrowth.

25. An implant according to claim 23 or 24
wherein the polymer material means includes Ultra High Molecular Weight Polyethylene.

26. An implant according to claim 23 or 24
wherein the polymer material means includes Polypropylene.

27. An implant according to claim 23 or 24
wherein the polymer material means includes High Density Polyethylene.

28. An implant according to claim 23 or 24
wherein the polymer material means includes Polyurethane Elastomer.

* * * * *